(12) United States Patent
Stasz

(10) Patent No.: US 7,608,047 B2
(45) Date of Patent: Oct. 27, 2009

(54) REUSABLE SNORE/AIR FLOW SENSOR

(75) Inventor: Peter Stasz, Moundsview, MN (US)

(73) Assignee: Dymedix Corporation, Shoreview, MN (US)

( * ) Notice: Subject to any disclaimer, the term of this patent is extended or adjusted under 35 U.S.C. 154(b) by 63 days.

(21) Appl. No.: 11/484,453

(22) Filed: Jul. 11, 2006

(65) Prior Publication Data
US 2007/0012089 A1 Jan. 18, 2007

Related U.S. Application Data

(60) Provisional application No. 60/700,365, filed on Jul. 18, 2005.

(51) Int. Cl.
*A61B 5/08* (2006.01)
(52) U.S. Cl. .................. 600/529; 600/538; 600/537
(58) Field of Classification Search ................ 600/529, 600/532–534, 537–538, 484; 73/862.046, 73/862.46, 862.68, 31.01, 721; 29/25.35, 29/855–858; 128/848
See application file for complete search history.

(56) References Cited

U.S. PATENT DOCUMENTS

| | | | | |
|---|---|---|---|---|
| 4,777,963 | A * | 10/1988 | McKenna ................... | 600/537 |
| 5,131,401 | A | 7/1992 | Westenskow et al. | |
| 5,161,541 | A * | 11/1992 | Bowman et al. ............ | 600/537 |
| 5,311,875 | A | 5/1994 | Stasz | |
| 5,413,111 | A | 5/1995 | Wilkinson | |
| 5,571,973 | A | 11/1996 | Taylot | |
| 5,827,198 | A * | 10/1998 | Kassal ........................ | 600/528 |
| 6,254,545 | B1 | 7/2001 | Stasz et al. | |
| 6,485,432 | B1 | 11/2002 | Stasz et al. | |
| 6,491,642 | B1 | 12/2002 | Stasz | |
| 6,551,256 | B1 | 4/2003 | Stasz et al. | |
| 6,894,427 | B2 | 5/2005 | Alfini | |
| 2003/0194523 | A1 * | 10/2003 | Kume et al. ................ | 428/40.1 |
| 2003/0236467 | A1 | 12/2003 | Alfini | |
| 2005/0096560 | A1 | 5/2005 | Alfini et al. | |
| 2005/0227082 | A1 * | 10/2005 | Shimazu et al. ............. | 428/413 |
| 2006/0000472 | A1 * | 1/2006 | Fenton .................. | 128/200.24 |
| 2007/0203558 | A1 * | 8/2007 | Jonsen et al. ............... | 607/142 |
| 2009/0000616 | A9 * | 1/2009 | Fenton .................. | 128/200.24 |
| 2009/0054792 | A1 * | 2/2009 | Sato et al. ................... | 600/484 |

FOREIGN PATENT DOCUMENTS

| | | |
|---|---|---|
| GB | 2116871 | 5/1986 |
| GB | 2192460 | 1/1988 |
| JP | 02291169 | 11/1990 |

* cited by examiner

*Primary Examiner*—Charles A Marmor, II
*Assistant Examiner*—Navin Natnithithadha
(74) *Attorney, Agent, or Firm*—Thomas J. Nikolai; Nikolai & Mersereau, P.A.

(57) ABSTRACT

A sensor for use with a polysomnograph in a sleep lab setting is made reusable by laminating a PVDF film and associated lead contacts within a flexible, moisture-impervious plastic envelope that is hermetically sealed about its periphery. Lead terminals within the envelope are adhered to the metalized surfaces of the PVDP film using a conductive adhesive which inhibits dislodgement of the leads from the sensor even with rough handling and cleaning.

6 Claims, 3 Drawing Sheets

REUSABLE SNORE/AIR FLOW SENSOR

CROSS-REFERENCE TO RELATED APPLICATIONS

This application claims priority to Provisional Application Ser. No. 60/700,365, filed Jul. 18, 2005, the contents of which are hereby incorporated by reference.

BACKGROUND OF THE INVENTION

1. Field of the Invention

This invention relates generally to apparatus for monitoring respiratory activity, which also can include snoring activity, and more particularly to a reusable pyro/piezo transducer for producing an electrical signal proportional to respiratory airflow and/or vibration due to snoring episodes for subjects undergoing sleep studies.

2. Discussion of the Prior Art

Applicant's assignee, Dymedix Corporation of Minneapolis, Minn., has pioneered the development of improved sensors that are adapted to be attached to the upper lip or throat area of a patient that, during sleep, produces an electrical signal proportional to inspiratory and expiratory airflow and to episodes of snoring. In U.S. Pat. No. 5,311,875, applicant first disclosed such a sensor embodying a polyvinylidene fluoride (PVDF) film as the active element of such a respiration activity sensor. The film has both pyroelectric and piezoelectric properties and, as such, is responsive to both temperature changes and physical vibration, producing an electrical signal output that can be signal processed to effectively separate the temperature change induced signal from the signal due to vibration.

Improvements in the sensor are the subject of U.S. Pat. Nos. 6,894,427, 6,551,256, 6,485,432, 6,491,642 and 6,254,545, the teachings of which are hereby incorporated by reference as if set forth in full herein.

For the most part, the sensor construction described in the aforereferenced patents were intended for single-use application in that they would not hold up to repeated cleaning. More particularly, moisture could permeate the layered construction to compromise the electrical interface between the PVDF film and its connection to an electrical lead. Moreover, the handling during cleaning operations would lead to detachment of the lead's contact with the PVDF film.

It is accordingly a principal object of the present invention to provide a respiratory activity sensor especially constructed so as to be reusable. More particularly, the sensor or transducer of the present invention is designed to be moisture impervious and constructed such that lead wire pull-out is no longer a problem.

SUMMARY OF THE INVENTION

In fabricating the sensor of the present invention, a sandwiched construction is employed in which a PVDF film is coated on its opposed major surfaces with a conductive layer and a pair of lead wires having a metal tab attached to the distal ends thereof are positioned on opposite sides of the PVDF film using a carbon-laced adhesive as a conductive bonding agent between the lead wire's metal tabs and the conductive coating on the PVDF film.

The PVDF film with the lead contact tabs affixed to its opposed major surfaces are sandwiched between upper and lower layers of double-sided adhesive tape that adhere to the film layer, to a portion of the leads and to one another. Next, a polyurethane film layer is adhered to the exposed sides of the double-sided tape. The polyurethane layers extend beyond the perimeter edges of the double-sided tape and the edge portions of the polyurethane layers are heat sealed to one another to totally encapsulate the PVDF film, the lead tabs and the layers of double-sided adhesive tape in a moisture-proof manner.

DESCRIPTION OF THE PREFERRED EMBODIMENT

Figure 1:
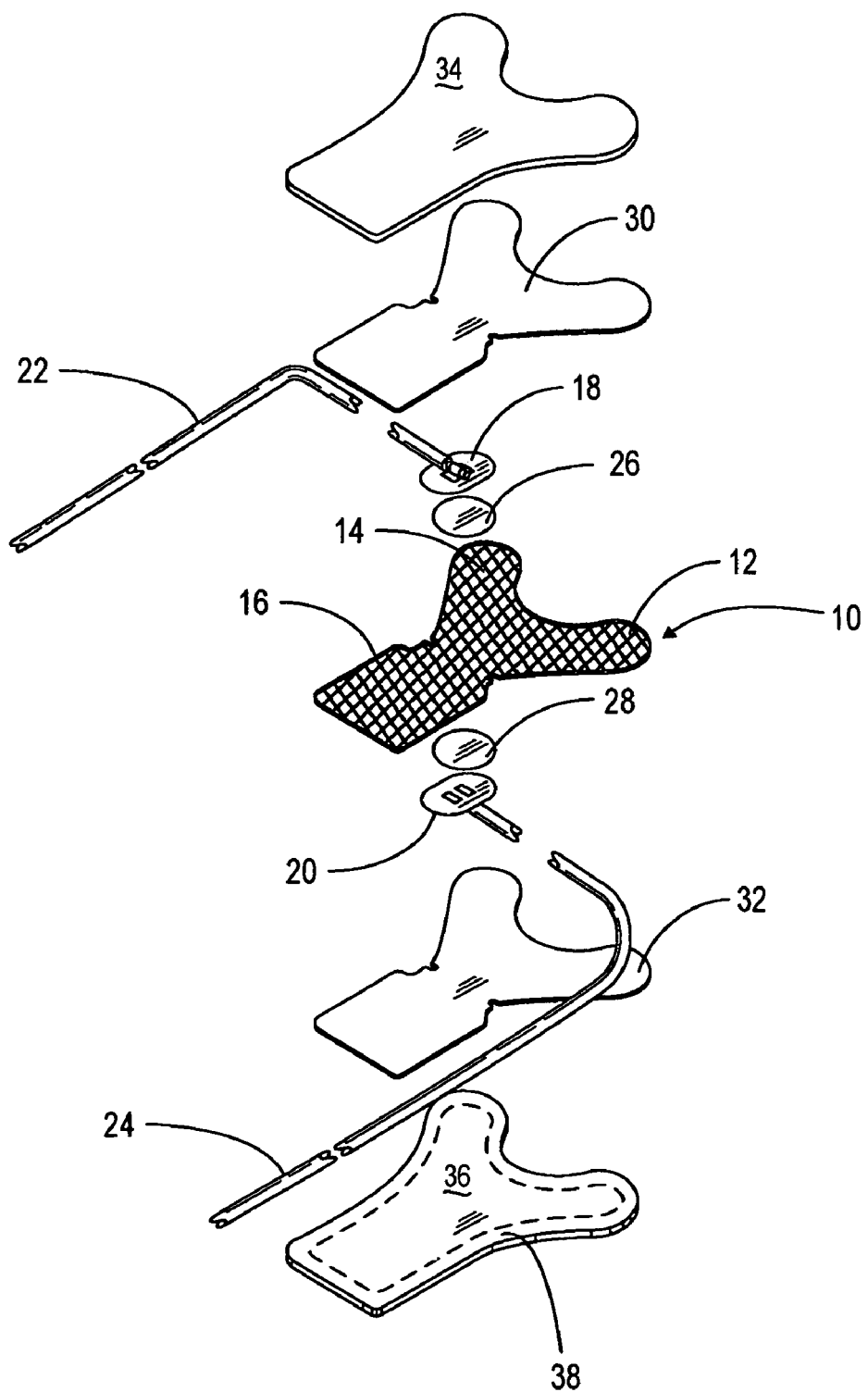
FIG. 1 is an exploded view of the reusable sensor constructed in accordance with a first embodiment of the invention.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Figure 2:
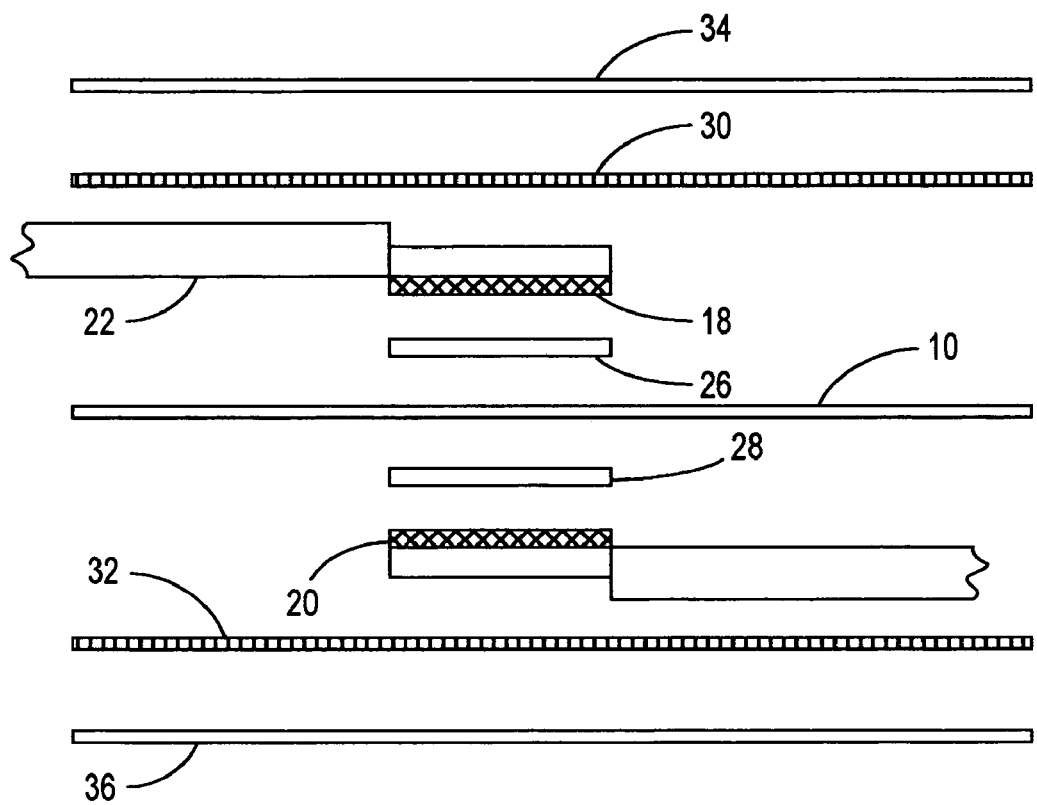
FIG. 2 is an expanded edge view of the embodiment of FIG. 1.

Referring to FIGS. 1 and 2, there is shown an exploded perspective view and an exploded edge view of a reusable airflow sensor especially designed for use with a polysomnograph in a sleep lab setting. The sensor comprises as its active element a polarized PVDF film layer 10 that, in the embodiment of FIG. 1, is somewhat Y-shaped having rounded lobes 12, 14, diverging from one another at a predetermined angle and a stem portion 16. The PVDF film layer 10 includes metallization layers on opposed major surfaces thereof represented by the cross-hatching thereon. The metallization layers serve to collect the charge produced by the PVDF film due to respiratory air flow impinging on the transducer or due to temperature change.

Affixed to the opposed major surfaces of the stem portion 16 are conductive electrode tabs 18 and 20 that are crimped and/or soldered to the exposed ends of insulated lead wires 22 and 24, respectively. To insure intimate contact between the conductive electrodes 18 and 20 and the metalized surfaces of the PVFD film 10, a conductive adhesive, such as that sold under the trademark ARclad® by Adhesives Research, Inc., is used. This material comprises an adhesive that is laced with conductive carbon particles that serves as a bonding agent between the electrodes 18 and 20 with the metalized layers adhered to the PVDF film. The ARclad® adhesive is represented in FIG. 1 by references numerals 26 and 28.

Pyro/piezo transducers of the type described can be procured from Measurement Specialties, Inc. of Morristown, Pa., with leads already attached to the metalized PVDF film, but the film shape is of one type—rectangular—and of a standard size.

First and second double-sided adhesive tape layers 30 and 32 cut to conform to the shape of the PVDF layer 10 are adhered to the opposed surfaces of the film layer 10 helping to secure the tab electrodes 18 and 20 and a portion of the wire leads 22 and 24 leading to the conductive tabs in place. Completing the assembly are first and second layers 34 and 36 of polyurethane film that are also cut to be of generally the same shape as the PVDF layer 10, but larger in size than the adhesive tape layers 30 and 32. During assembly, the polyurethane plastic layer 34 is adhered to the exposed adhesive surface of the double-sided tape layer 30. Likewise, the polyurethane plastic layer 36 is bonded to the exposed adhesive on the tape layer 32.

Because the polyurethane plastic layers 34 and 36 are of a larger area than the tape layers 30 and 32, a perimeter portion 38 extends beyond the edges of the tape layers 30 and 32. The perimeter portions of the polyurethane layers 34 and 36 are brought into contact with one another and fused together in a thermal bonding process. As a result, the interior components sandwiched between the outer polyurethane plastic layers 34 and 36 are fully encapsulated and thereby sealed against ingress of moisture even when exposed to cleaning solutions and sterilants. Also, because of the manner in which the electrode tabs 18 and 20 are adhered to the PVDF layer 10 by the ARclad® conductive adhesive and the way in which the portion of the leads leading thereto are adhesively attached to the tape layers 30 and 32, testing has shown that the wire leads 22 and 24 will break before the electrodes will pull free from the sensor assembly.

While polyurethane film is preferred for the outer layers 34 and 36, because it is heat-sealable and hydrophobic, other non-porous heat sealable plastic materials may also be used to encapsulate the PVDF and the distal ends of the lead wires.

In use, the sensor of FIG. 1 is placed on the upper lip of a subject such that the lobes 12 and 14 are proximate the nasal openings and the stem portion 16 extends beyond the upper lip. Sensor 10 is held in place on the lip by means of a suitable adhesive or by using a strip of adhesive tape. Changes in temperature due to inspiratory and expiratory airflow that impinges on the sensor produce an output signal component proportional to the temperature swings. Should there be episodes of snoring, the sensor that is in contact with the skin, will sense the snoring vibration and the piezoelectric properties of the PVDF will result in a second signal component that varies with the intensity of the snoring. These signals are fed to a polysomnograph instrument where signal processing circuitry is used to separate the pyro signal from the piezo signal.

Figure 3:
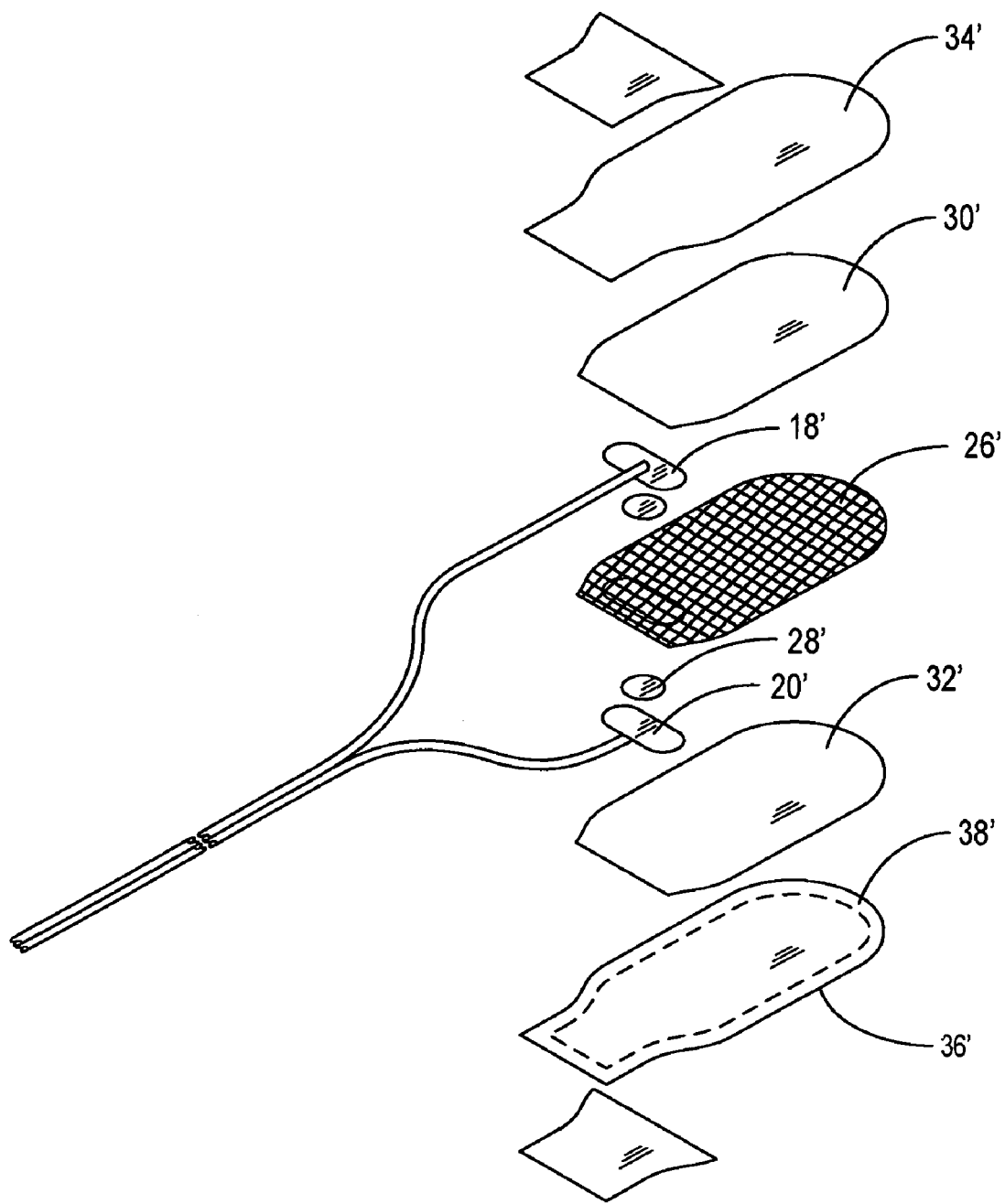
FIG. 3 is an exploded view of an alternative embodiment of a snore sensing element made in accordance with the present invention.

Turning next to FIG. 3, there is shown an alternative embodiment especially designed for attachment to the throat area of a sleeping patient in a sleep lab environment. This sensor is also reusable in that it can be cleaned. It is substantially identical in its construction to the embodiment as illustrated in FIGS. 1 and 2 and corresponding numbers, only primed, are applied to the embodiment of FIG. 3. The only difference between the embodiments of FIG. 1 and FIG. 3 is the shape of the sensor. In that the constructional details have already been explained in connection with the embodiment of FIGS. 1 and 2, it is felt unnecessary to repeat it in connection with the embodiment of FIG. 3.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A reusable snore/air flow sensor comprising:
   (a) a polyvinylidene fluoride (PVDF) film of a predetermined shape configuration and having a layer of metallization on opposed major surfaces of said film;
   (b) a first and a second insulated lead wires each having a contact member affixed to an uninsulated end portion thereof;
   (c) a conductive adhesive adhering the contact members on the first and the second lead wires to the layers of metallization of the opposed major surfaces of the PVDF film;
   (d) a first layer of double-sided adhesive tape, the layers being of said predetermined shape configuration and overlaying said contact members and a portion of the insulated lead wires and adhered on a first side to the metalized PVDF film, forming a contiguous seal with the adhesive tape;
   (e) a second layer of double-sided adhesive tape, the layers being of said predetermined shape configuration and overlaying said contact members and a portion of the insulated lead wires and adhered on a second side to the metalized PVDF film, forming a contiguous seal with the surface of the adhesive tape; and
   (f) a first and a second outermost layers of a moisture impervious, flexible, thermoplastic material, the first outermost layer being adhered to the first layer of double-sided adhesive tape, forming a contiguous seal with the surface of the adhesive tape, and the second outermost layer being adhered to the second layer of double-sided adhesive tape, forming a contiguous seal with the surface of the adhesive tape, and with perimeter portions of the first and second outermost layers being bonded to one another forming a non-porous permanent encapsulation.

2. The reusable snore/air flow sensor of claim 1 wherein the predetermined shape configuration is generally Y-shaped.

3. The reusable snore/air flow sensor of claim 1 wherein the predetermined shape configuration is generally rectangular, but with a rounded end.

4. The reusable snore/air flow sensor as in claim 1 wherein the conductive adhesive is a pressure sensitive adhesive containing conductive carbon particles.

5. The reusable snore/air flow sensor as in claim 1 wherein the first and second outermost layers comprise polyurethane.

6. The reusable snore/air flow sensor as in claim 1 wherein the bonded perimeter portion of the first and second outermost layers preclude moisture form penetrating the sensor.

* * * * *